United States Patent [19]

Chevallet et al.

[11] Patent Number: 5,227,049
[45] Date of Patent: Jul. 13, 1993

[54] SINGLE-NEEDLE CIRCUIT FOR CIRCULATING BLOOD OUTSIDE THE BODY IN BLOOD TREATMENT APPARATUS

[75] Inventors: Jacques Chevallet, Serezin du Rhone; Jean-Claude Riquier, Rilleux, both of France; Carl-Henry Örndal, Eslöv; Allan Petersen, Bjärred, all of Sweden

[73] Assignee: Hospal Industrie, France

[21] Appl. No.: 743,037

[22] Filed: Aug. 9, 1991

[30] Foreign Application Priority Data

Aug. 20, 1990 [SE] Sweden .............................. 90027004
Feb. 6, 1991 [FR] France ................................ 91 01565

[51] Int. Cl.$^5$ .......................... B01D 61/00; A61M 1/00
[52] U.S. Cl. ........................................ 210/97; 210/86;
  210/87; 210/90; 210/104; 210/134; 210/137;
  210/143; 210/195.2; 604/4; 604/5
[58] Field of Search .................... 210/86, 87, 90, 97,
  210/101, 321.6, 102, 104, 116, 134, 137, 195.2,
  141, 143, 416.1; 604/4, 5, 6; 422/44

[56] References Cited

U.S. PATENT DOCUMENTS

| 3,964,479 | 6/1976 | Boag et al. | 210/90 |
| 4,372,846 | 2/1983 | Yamagami et al. | 210/87 |
| 4,486,303 | 12/1984 | Brous | 210/87 |
| 4,554,069 | 11/1985 | Aid et al. | 210/101 |
| 4,596,550 | 6/1986 | Troutner | 604/5 |
| 4,614,590 | 9/1986 | Rath et al. | 210/90 |
| 4,643,714 | 2/1987 | Brose | 604/4 |
| 4,650,458 | 3/1987 | Dahlberg et al. | 604/5 |
| 4,758,336 | 6/1988 | Bock et al. | 604/5 |
| 4,776,837 | 10/1988 | Kopp | 604/4 |
| 4,935,125 | 6/1990 | Era et al. | 210/321.71 |
| 4,997,570 | 3/1991 | Polaschegg | 210/646 |

FOREIGN PATENT DOCUMENTS

| 0104897A2 | 9/1983 | European Pat. Off. . |
| 0104895 | 4/1984 | European Pat. Off. | 604/5 |
| 0148319A1 | 8/1984 | European Pat. Off. . |
| 0229271A2 | 11/1986 | European Pat. Off. . |

Primary Examiner—Robert A. Dawson
Assistant Examiner—Sun Uk Kim
Attorney, Agent, or Firm—Finnegan, Henderson, Farabow, Garrett & Dunner

[57] ABSTRACT

A blood treatment apparatus having a circuit for circulating blood outside the body and designed to be connected to a patient via a single needle, including a blood treatment device such as a heamodialyzer, pumps for causing blood to flow through the circuit, a first blood expansion chamber located in the circuit upstream of the blood treatment device for temporarily storing a volume of blood to be treated, a second blood expansion chamber located downstream of the blood treatment device for temporarily storing a volume of treated blood, first and second pressure regulators, connected to the first and second blood expansion chambers, for adjusting pressure in the blood expansion chambers, and a controller for interacting with the regulators to maintain a substantially constant pressure in each of the first and second chambers during a treatment session.

27 Claims, 4 Drawing Sheets

SINGLE-NEEDLE CIRCUIT FOR CIRCULATING BLOOD OUTSIDE THE BODY IN BLOOD TREATMENT APPARATUS

BACKGROUND OF THE INVENTION

1. Field of the Invention

The present invention relates to blood treatment apparatus including a circuit for circulating blood outside the body and designed to be connected to a patient via a single needle or "cannula", this apparatus being, for example, an artificial kidney, a plasmapheresis apparatus or a blood oxygenation apparatus.

2. Description of the Related Art

With such apparatuses, it is conventional for the circuit for circulating blood outside the body to be connected to the patient either by means of two needles with blood being withdrawn from the patient and returned to the patient simultaneously via respective ones of the needles, or else via a single needle with blood then being withdrawn and returned alternatively via the single needle.

The advantage of making a connection by means of a single needle is that it halves the number of punctures that need to be made through the skin of the patient, and with chronic treatments such as dialysis for kidney failure, this may be of crucial importance since access points to the blood in a human body are limited in number and need to be used sparingly.

However, the way in which a single-needle blood treatment apparatus operates suffers from drawbacks because of the need during each withdrawal and return cycle to store a volume of blood in the circuit outside the body, with the stored volume being at least as great as the volume actually treated during the cycle. This need does not arise when the circuit for circulating blood outside the body is connected to the patient via two needles, since blood flows continuously therethrough.

As a matter of fact, in present circuits adapted for operation with a single needle, this volume of blood is generally stored both before and after treatment (in some circuits, after treatment only) in two expansion chambers disposed respectively upstream and downstream from the blood treatment device proper (hemodialyzer, oxygenator, etc.), with the apparatus as a whole giving rise, in operation, to different and varying pressures in said chambers, thereby giving rise to varying pressure differences and, where applicable, to varying flow rates through the treatment device.

Unfortunately, depending on the type of treatment device such pressure variations may be most undesirable. This is particularly true of hemodialyzers in which pressure variations run the risk of rupturing the membrane, may give rise to undesired retrofiltration or ultrafiltration, and make it difficult or even impossible to control an ultrafiltration flow rate accurately when ultrafiltration is desired. As to the variations in blood flow rate through a hemodialyzer, they give rise to reduced performance, and in particular to a loss of renal clearance.

SUMMARY OF THE INVENTION

An object of the invention is to improve existing single-needle blood treatment apparatuses in order to optimize operation thereof.

According to the present invention, this object is achieved by providing a blood treatment apparatus comprising a circuit for circulating blood outside the body and designed to be connected to a patient via a single needle, said circuit including a blood treatment device proper, blood circulation means for causing blood to flow through the circuit, and at least one blood expansion chamber, the apparatus being characterized in that it includes pressure regulation means for maintaining an adjustable pressure substantially constant at least downstream from the blood treatment device.

In a first embodiment of the present invention, the pressure regulation means comprise pumping means connected to the expansion chamber to act on the gas pressure in the expansion chamber.

In a second embodiment of the present invention, the pressure regulation means comprise means for varying the volume of the expansion chamber as a function of the variations of the volume of the liquid therein.

According to a characteristic of the present invention, the means for varying the volume of the expansion chamber comprise a variable-volume chamber which is closed relative to the atmosphere and connected to the expansion chamber, together with actuator means for varying the volume of the variable-volume chamber as a function of the variations in the volume of liquid in the expansion chamber. Advantageously, the variable volume chamber includes a moving wall which is subjected to reciprocating displacement by the actuator means with the direction of displacement being reversed simultaneously with the changeover from withdrawing blood from a patient to returning blood to the patient and vice versa. Preferably, the actuator means comprise a rotary motor connected to the moving wall of the variable volume chamber by a connecting rod.

In a variant of this second embodiment of the invention, the apparatus include two blood expansion chambers disposed respectively upstream and downstream of the blood treatment device and, in operation, the pressures in the upstream and downstream expansion chambers are respectively lower than and higher than atmospheric pressure. The means for varying the volume of the expansion chambers comprise two variable volume bellows chambers closed to the atmosphere and connected to respective ones of the expansion chambers, and means balanced about a pivot to provide mechanical coupling with the bellows chambers.

BRIEF DESCRIPTION OF THE DRAWINGS

Other characteristics and advantages of the present invention appear from reading the following description. Reference is made to the accompanying drawings, in which.

DESCRIPTION OF THE PREFERRED EMBODIMENTS

Figure 1:
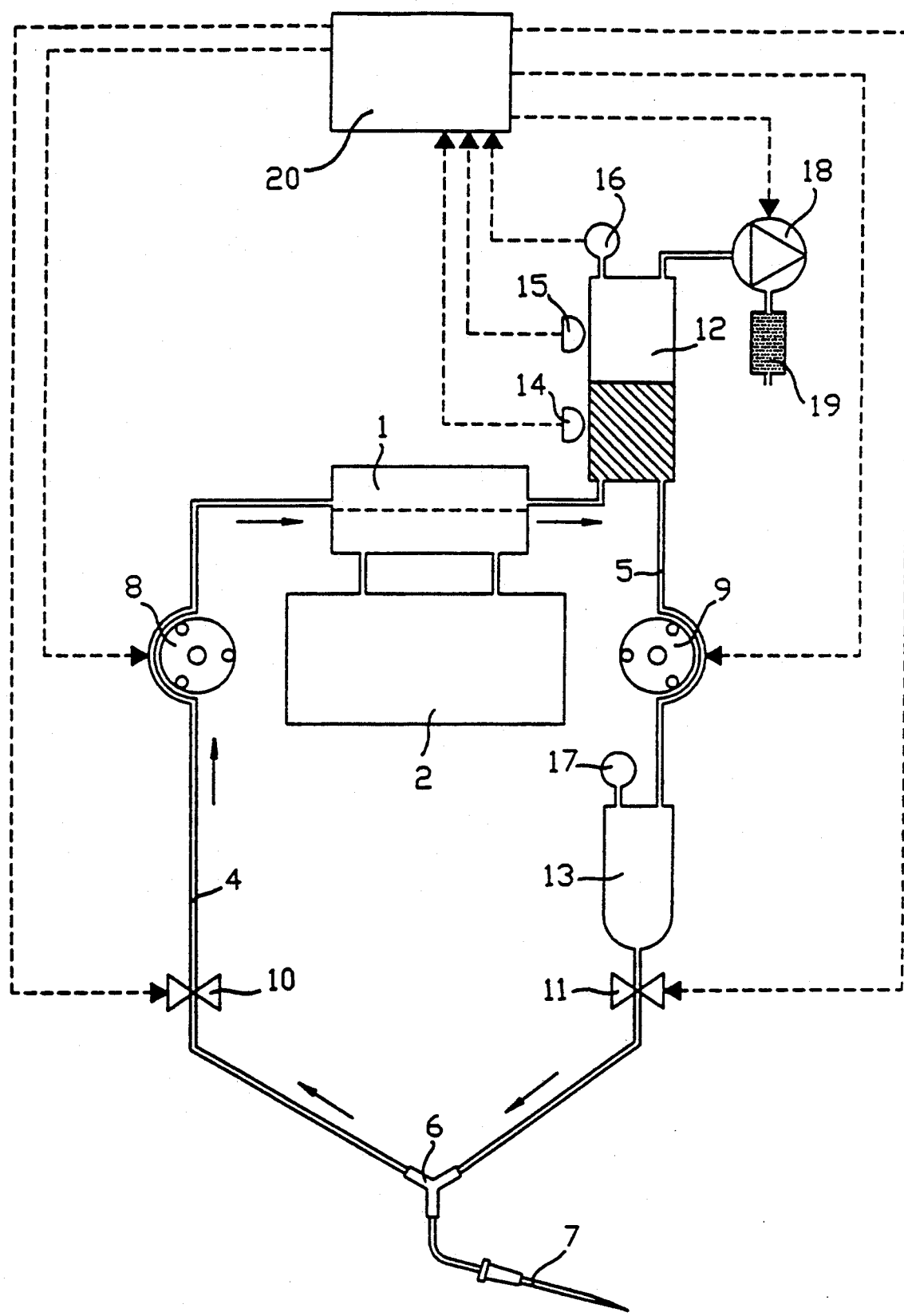
FIG. 1 is a diagram of a first circuit of the invention for circulating blood outside the body.

The circuit shown in FIG. 1 for circulating blood outside the body comprises a blood treatment device 1, e.g. a hemodialyzer, having a blood inlet and a blood outlet which are connected respectively to an upstream duct 4 and to a downstream duct 5, which ducts are interconnected at their opposite ends by a Y-junction 6 whose third path is itself connected to a needle 7 for inserting in a blood vessel of a patient. The hemodialyzer 1 is also connected to a dialysis monitor 2 via its dialysate inlet and outlet.

Each of the upstream and downstream ducts 4 and 5 is provided with a respective occlusive pump 8, 9 and a respective clamp 10, 11, with the clamps 10 and 11 being disposed immediately downstream and upstream from the Y junction 6. The downstream duct 5 further includes a blood expansion chamber 12 disposed between the hemodialyzer 1 and the pump 9, and a bubble trap 13 disposed between the pump 9 and the clamp 11. The expansion chamber 12 is fitted with two liquid detectors 14 and 15 respectively for identifying a low level and a high level which delimit between them a volume corresponding to the volume of blood that is treated during one operating cycle of the circuit, as explained below. In addition, both the expansion chamber 12 and the bubble trap 13 are provided with respective pressure sensors 16 and 17.

In accordance with the invention, the circuit for circulating blood outside the body includes pressure regulation means enabling a constant determined pressure to be established and maintained in the circuit downstream from the hemodialyzer 1. In a preferred embodiment, the regulation means includes a pump 18 connected to the top of the expansion chamber 12 and which is connected to the atmosphere via a sterile filter 19. The pump 18 is suitable both for lowering pressure and for raising pressure and it is controlled by a control unit 20 as a function of a comparison between a previously recorded reference value and the pressure value as measured by the sensor 16, with the pump 18 being controlled in such a manner as to cause the measured value to tend at all times towards the reference value.

The circuit operates cyclically, with each cycle comprising a stage during which blood to be treated is withdrawn from the patient and a stage during which treated blood is returned to the patient, with the volume of blood treated during each cycle corresponding substantially to the volume delimited between the two liquid detectors 14 and 15 in the expansion chamber 12. The withdrawing stage is initiated at the end of the preceding cycle when the level of blood in the expansion chamber drops to a level where it is no longer detected by the liquid detector 14 which marks a low level. The downstream pump 9 which was in operation at the end of the preceding cycle is then stopped, thereby shutting off the downstream duct 5. Simultaneously, the upstream pump 8 is switched on, and blood passes through the hemodialyzer 1 causing the level in the expansion chamber 12 to rise. As a result the gas pressure begins to rise and this is detected by the pressure sensor 16, causing the pump 18 to be switched on to pump air out from the expansion chamber 12, thereby maintaining a constant pressure therein equal to the reference pressure. When the blood level reaches liquid detector 15, marking a high level, the upstream pump 8 is stopped and the downstream pump 9 is started, thereby initiating the stage during which blood is returned to the patient. As a result the gas pressure in the expansion chamber 12 begins to drop, and this is detected by the sensor 16, causing the control unit 20 to switch on the pump 18 so as to deliver air to the chamber, thereby maintaining the pressure therein constant. The blood returning stage terminates when the blood level drops to the low liquid detector 14, whereupon a new cycle begins. In this embodiment, the clamps 10 and 11 are essentially for safety purposes, and in particular the clamp 11 is closed when the pressure in the bubble trap 13 falls below a determined value. However, in circuits where the duct length between the clamps and the pumps is relatively long, each of the clamps 10 and 11 may be opened and/or closed simultaneously with the pump 8 or 9 situated on the same side of the hemodialyser being switched on and off, thereby reducing blood recirculation.

Figure 2:
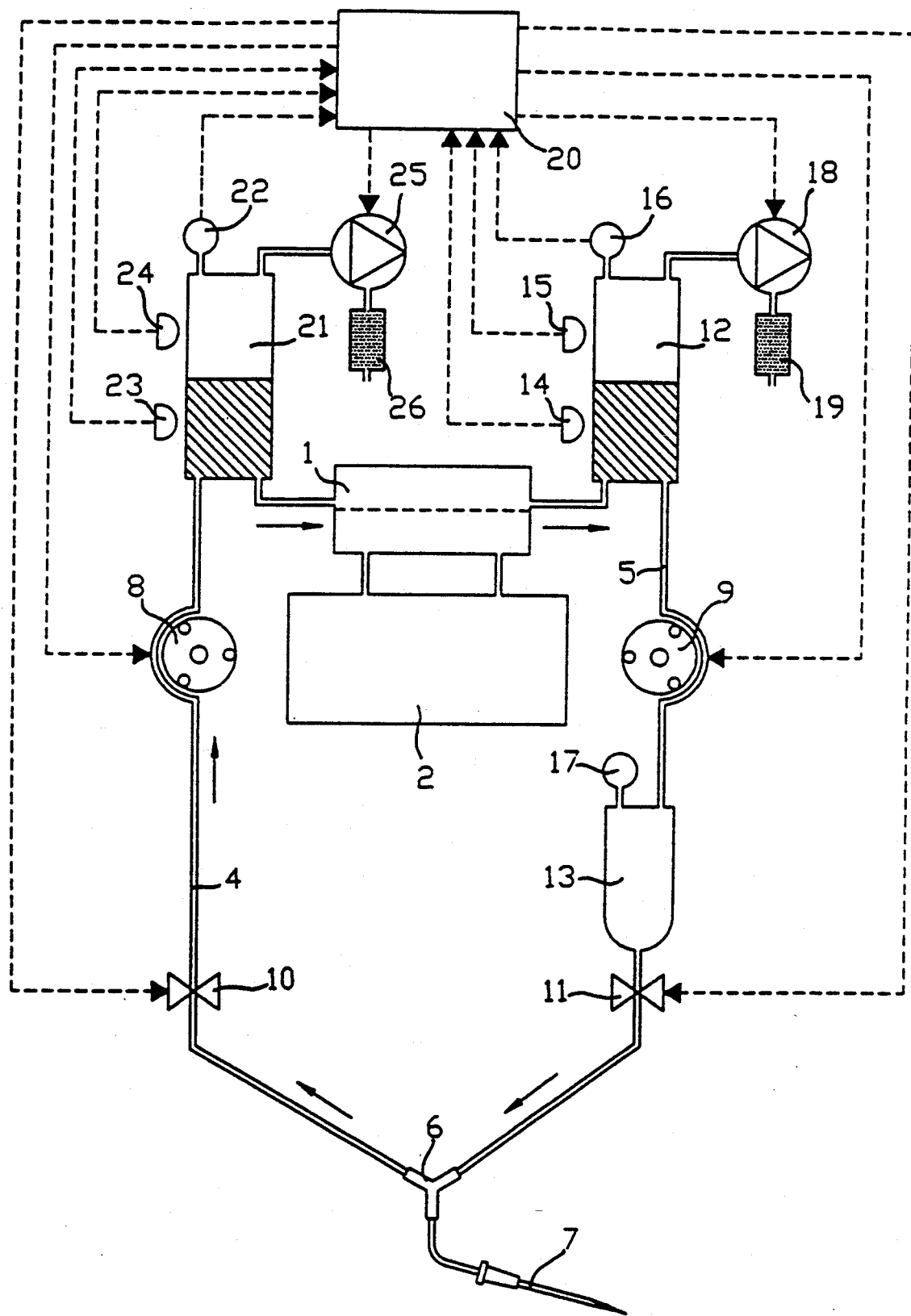
FIG. 2 is a diagram of a second circuit of the invention for circulating blood outside the body.

The circuit for circulating blood outside the body as shown in FIG. 2 differs from that described above in that it includes two expansion chambers instead of only one, with the duct 4 upstream from the hemodialyzer 1 being provided with an expansion chamber 21 between the circulation pump 8 and the hemodialyzer. Like the chamber 12, the chamber 21 is fitted with a pressure sensor 22 and with two liquid detectors 23 and 24 which delimit between them the half of the volume of blood treated during each operating cycle of the circuit. A pump 25 connected to the top of the expansion chamber 21 and also to the atmosphere via a sterile filter 26 enables a determined constant pressure to be maintained upstream from the hemodialyzer 1.

During initial rinsing and filling of the circuit, i.e. prior to blood treatment proper, the pressures upstream and downstream of the hemodialyzer 1 are adjusted to determined values selected as a function of a certain number of parameters (and in particular the characteristics of the hemodialyzer, and the desired blood flow rate through the circuit). These values are also recorded in the control unit 20 as reference values. Given the way in which the circuit is operated (as described below), the pressure upstream from the hemodialyzer 1 is greater than the pressure downstream therefrom, with these two pressures being maintained substantially constant throughout a dialysis session. The pressure difference inside the hemodialyzer thus remains constant, as does the rate at which blood flows through it.

This circuit operates as follows. When the level of blood in both expansion chambers 12 and 21 is low, the stage during which blood is withdrawn from the patient is initiated by stopping the downstream pump 9 and simultaneously starting the upstream pump 8 (which pumps were respectively running and stopped during the preceding stage). Since the downstream duct 5 is shut off by the occlusive pump 9, operation of the upstream pump 8 withdrawing blood from the patient and delivering it to the hemodialyzer 1 tends to raise the pressure in both expansion chambers 12 and 21. This is detected in the control unit 20 by comparing the pressures measured by the pressure sensors 16 and 22 with the corresponding reference values as stored initially. The control unit 20 then causes the pressure regulation pumps 18 and 25 to take air from the chambers so as to maintain a constant pressure in each of the expansion chambers 12 and 21. The blood to be treated is delivered by the pump 8 to the upstream expansion chamber 21 and it is expelled therefrom by the pressure difference that exists between the expansion chambers, thereby causing blood to flow at a constant rate through the dialyzer 1, with treated blood filling the expansion chamber 12. When blood reaches the high level in the expansion chambers 12 and 21, the stage of withdrawing blood from the patient is stopped and simultaneously the stage of returning blood to the patient is initiated. The upstream pump 8 is stopped and simultaneously the downstream pump 9 is started, and since the pump 8 shuts off the upstream duct 5, this tends to cause the pressure in the expansion chambers 12 and 21 to drop. The control unit 20 then causes the pressure regulation pumps 18 and 25 to operate in the opposite direction, or if they were not operating, it causes them to pump air into the chambers so as to maintain the pressures therein constant. The treated blood present in the downstream expansion chamber 12 is delivered to the patient by the downstream pump 9, at the pumping rate of this pump, while the non-treated blood present in the upstream expansion chamber 21 is expelled by the pressure difference that exists between the expansion chambers 12 and 21 so as to flow through the hemodialyzer 1 and thus into the downstream expansion chamber 12. When the blood in the expansion chambers 12 and 21 has dropped to the low level, then the stage during which blood is returned to the patient comes to an end and simultaneously the following blood-withdrawing stage is initiated.

In the process described above, it will be observed that the upstream and downstream circulation pumps 8 and 9 serve respectively not only to withdraw blood from and to return blood to the patient at a constant flow rate, but also keep up the pressures initially created in the expansion chambers 12 and 21, which pressures are maintained substantially constant by the pressure regulation pumps 18 and 22. It will also be observed that it is the pressure difference between the chambers 12 and 21 that drives blood from one chamber to the other at a constant flow rate, which flow rate depends both on the pressure difference and on the head losses in the hemodialyzer 1.

Figure 3:
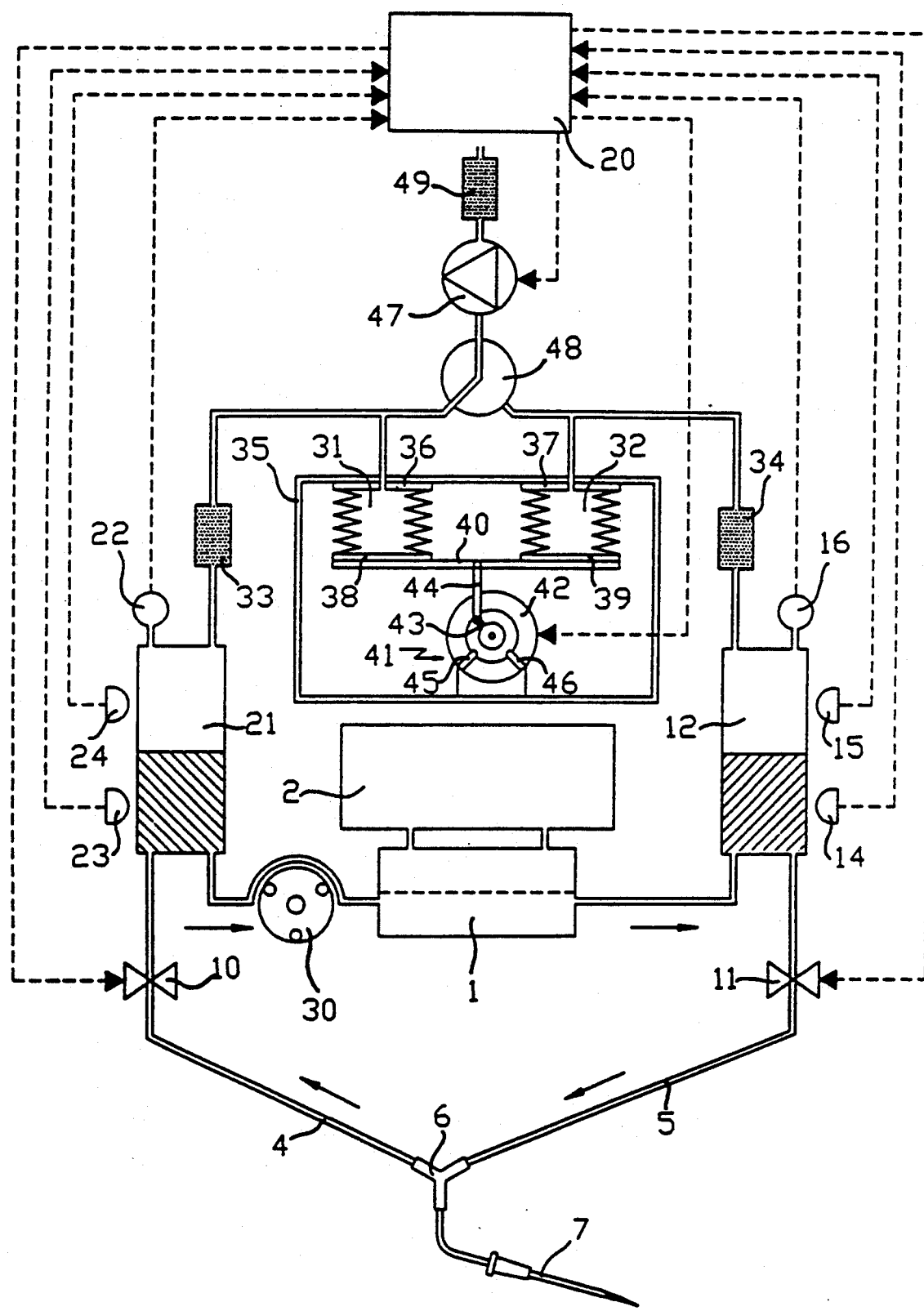
FIG. 3 is a diagram of a third circuit of the invention for circulating blood outside the body.

The circuit shown in FIG. 3 for circulating blood outside the body differs from that described with reference to FIG. 2 essentially in that it includes only one circulation pump 30 which is disposed on the upstream duct 4 between the expansion chamber 21 and the hemodialyzer 1, and in that the means for regulating the pressure in the expansion chambers 12 and 21 are constituted by two variable-volume chambers 31 and 32 closed relative to the atmosphere and connected to respective ones of the expansion chambers 21 and 12 via sterile filters 33 and 34.

Each of the two variable volume chambers 31, 32 comprises a flexible bellows wall extending between a pair of opposite plane end walls 36, 38 and 37, 39 respectively. They are held in place by respective ones of their end walls 36 and 37 to a frame 35 in such a manner that the fixed walls 36 and 37 are substantially in the same plane. They are also mechanically coupled to each other via their respective other end walls 38 and 39 by means of a coupling element 40 mounted to move in a direction perpendicular to the fixed end walls 36 and 37 of the chambers 31 and 32.

An actuator member 41 is connected to the coupling element 40 to impart reciprocating motion thereto, i.e. both to compress and to expand the variable volume chambers 31 and 32. In the embodiment shown, the actuator member 41 comprises a motor 42 rotating a crank 43 connected to the coupling element 40 by means of a connecting rod 44. The motor 42 is caused to rotate the crank alternately in one direction and the in the other between two safety limit positions defined by end-of-stroke contacts 45 and 46 which are provided for switching off the motor 42 when the crank comes into abutment against one or other of them.

A occlusive pump 47 for establishing pressure is selectively connectable to one or other of the expansion chambers 12 and 21 via a selector valve 48 and, on the other hand, is connected to the atmosphere via a sterile filter 49. This pump 47 serves to establish the desired pressures in each of the expansion chambers 12 and 21 before beginning blood treatment proper, and also serves in operation to correct existing pressures in the event of pressure drifting, thereby returning them to their initial pressure levels, i.e. to reference pressures recorded in the control unit 20.

This circuit operates as follows. The circulation pump 30 runs continuously, with switching between the blood-withdrawing and the blood-returning stages during successive cycles being obtained by simultaneously changing the (open/closed) position of the clamps 10 and 11, with these clamps always being in phase opposition. Given the position of the circulation pump 30 relative to the expansion chambers 12 and 21, the pressure in the upstream chamber 21 is always lower than atmospheric pressure and the pressure in the downstream chamber 12 is always above atmospheric pressure, with these pressures being adjusted during initial filling of the circuit to determined values that are also recorded in the control unit 20 as reference values. For reasons that appear below, the magnitudes of these values are preferably selected to be as large as possible given the strength of the ducts 4 and 5, the acceptable pressure difference across the hemodialyzer 1, and the risks of blood hemolysis in the needle 7 when the rate of flow of blood therethrough becomes too high.

The stage during which blood is withdrawn from the patient is initiated when the previously-open clamp 11 is closed simultaneously with the previously-closed clamp 10 being opened. Under the effect of the reduced pressure in the upstream expansion chamber 21, the blood to be treated is sucked into this chamber and it is drawn in at a constant flow rate since, as the level of the blood inside both expansion chambers 12 and 21 rises, the actuator 41 expands the variable-volume chambers 31 and 32 correspondingly so that the pressures in the chambers remain substantially constant. The blood present in the upstream expansion chamber 21 is pumped out by the circulation pump 30 which delivers a substantially constant flow rate to the hemodialyzer 1, with purified blood leaving the hemodialyzer and accumulating in the downstream expansion chamber 12. When the blood reaches the high level in the expansion chambers 21 and 12, the clamp 10 is closed and simultaneously the clamp 11 is opened, thereby beginning the stage of returning blood to the patient.

Advantageously, for safety reason, the initiation of the blood-returning stage is controlled at the end of the blood-withdrawing stage as soon as blood is detected by either one of the high liquid detectors 15 and 24.

As soon as the clamp 11 is opened, under the effect of the raised pressure that exists inside the downstream expansion chamber 12, the purified blood is expelled towards the patient. This takes place at a substantially constant flow rate, as during the blood-withdrawing stage, since at the moment of stage change-over, the direction in which the actuator 41 operates is reversed so that the variable-volume chambers 31 and 32 are compressed to track the blood level dropping inside the expansion chambers 12 and 21.

In accordance with the invention, the direction of rotation of the motor 42 is reversed as follows: initially, the speed of rotation of the motor 42 is selected as a function of the speed of rotation of the circulation pump 30 so that the motor 42 rotates throughout each blood withdrawal or return stage. Under such normal operating conditions, the variation in volume of the bellows chambers 31 and 32 substantially tracks that of the blood in the expansion chambers 12 and 21 and the crank 43 does not come into abutment with the end-of-stroke contacts 45 and 46. These contacts are thus provided only for the event of the speed of the motor 42 drifting positively, in which case they prevent the motor turning through more than a single turn during any blood withdrawing or return stage, preventing the volume variations of the bellows chambers 31 and 32 getting out of phase with the volume variations of the blood in the expansion chambers 12 and 21, even to a small extent. Because of these end-of-stroke contacts, should the speed of the motor 42 increase undesirably, its rotation is stopped before the end of any blood withdrawing or return stage. In any event, the motor 42 is reversed (possibly from an already-stopped state) simultaneously with the clamps 10 and 11 being operated.

While purified blood is being returned to the patient, blood to be treated present in the upstream expansion chamber 21 is pumped by the circulation pump 30 and delivered to the hemodialyzer 1 so that purified blood enters the downstream expansion chamber 12 while said chamber is being emptied. When the blood level in both chambers reaches the low level, the positions of the clamps 10 and 11 are swapped over and a new cycle begins.

Advantageously, for safety reason, the initiation of the blood-withdrawing stage is controlled at the end of the blood-returning stage as soon as blood is no longer detected by either one of the low liquid detectors 14 and 23.

The pressure in each of the chambers is monitored and adjusted on a continuous basis by the control unit 20 which controls the pressurizing pump 47 to take air from or to deliver air to one or other of the expansion chambers 12 and 21 whenever the pressures measured in these chambers by the pressure sensors 16 and 22 move out from a range of initially-recorded reference values for each of the expansion chambers 12 and 21.

In the above-described process, it will be observed that in addition to causing blood to flow continuously through the hemodialyzer 1, the circulation pump 30 also keeps up the pressures initially established in the expansion chambers 12 and 21 by means of the pressurizing pump 47. It will also be observed that it is the reduced pressure in the upstream expansion chamber 21 and the increased pressure in the downstream expansion chamber 12 that serve respectively to withdraw blood from the patient and to return blood to the patient. It is therefore particularly advantageous to maintain these pressures constant and as different as possible from atmospheric pressure so as to obtain maximum flow rates when withdrawing blood and when returning blood, thereby reducing cycle duration to a minimum and thus minimizing the duration of a dialysis session.

Figure 4:
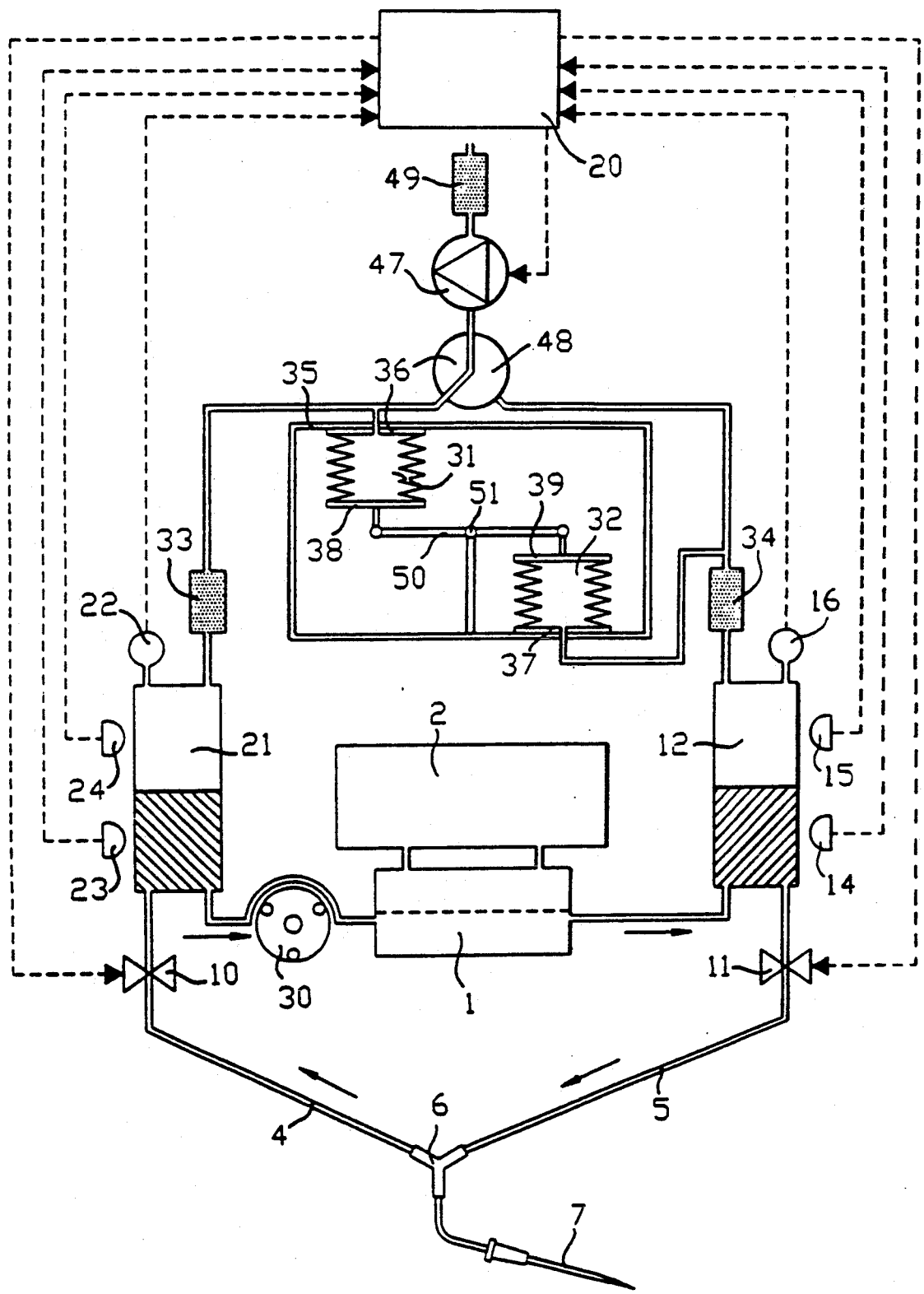
FIG. 4 is a diagram of a variant of the circuit shown in FIG. 3 for circulating blood outside the body.

The circuit shown in FIG. 4 for circulating blood outside the body differs from the circuit described with reference to FIG. 3 in that the means implemented for varying the volume of the bellows chambers 31 and 32 are simply constituted by a mechanical coupling, with the chambers each having one of their end walls 36, respectively 37, fixed to a fixed frame 35 so as to be situated on opposite sides of a balance arm 50 hinged about an pivot 51, with each end of the balance arm being connected by a hinge to the free end wall 38, respectively 39, of a corresponding one of the bellows chambers. The position of the pivot 51 along the balance arm 50 is selected as a function of the pressures that are selected for each of the expansion chambers 12 and 21 so that the traction exerted on the corresponding end of the balance arm 50 by the bellows chamber 31 in which pressure is reduced balances the thrust exerted on the other end of the balance arm by the bellows chamber 32 in which pressure is increased.

As a result, in operation, when the pressure in the expansion chamber 21 begins to drop continuously during the blood-returning stage because of the upstream clamp 10 being closed and because of blood being taken from this chamber by the circulation pump 30, this pressure drop is continuously compensated by the bellows chamber 31 being compressed by atmospheric pressure, and this compression acts via the balance arm 50 to compress the bellows chamber 32, thereby also keeping pressure constant in this chamber. Conversely, while blood is being withdrawn from the patient, when pressure begins to rise continuously in the expansion chamber 12 by virtue of the downstream clamp 11 being closed and blood being delivered to this chamber by the circulation pump 30, this pressure increase is continuously compensated by the bellows chamber 32 expanding, thereby acting via the balance arm 50 to expand the bellows chamber 31 and thus also maintain a constant pressure in said chamber.

The invention is not limited to the embodiments described above and numerous variants are possible. In particular, with the circuits shown in FIGS. 3 and 4, it is naturally possible for the fixed-volume expansion chambers 12 and 21 connected to the variable-volume chambers 31 and 32 to be replaced by variable-volume expansion chambers, which chambers could be provided with respective bellows in their upper portions, or could be constituted by bodies in the form of cylinders having pistons sliding in sealed manner therein to vary the inside volumes thereof.

Similarly, the pumps 18, 25, and 47 used in the circuits shown above for taking air from or delivering air to the expansion chambers 12 and 21 could be replaced by pumps for suction or delivery purpose associated with valves for putting these chambers into communication with the atmosphere.

What is claimed is:

1. A blood treatment apparatus having a circuit for circulating blood outside the body and designed to be connected to a patient via a single needle, the apparatus comprising:
   a blood treatment device;
   blood circulation means for causing blood to flow through the circuit;
   a first blood expansion chamber located in the circuit upstream of the blood treatment device for temporarily storing a volume of blood to be treated;
   a second blood expansion chamber located in the circuit downstream of the blood treatment device for temporarily storing a volume of treated blood;
   first and second pressure regulation means, respectively connected to the first and second blood expansion chambers, for adjusting pressure in the blood expansion chambers; and
   means for controlling the first and second pressure regulation means to maintain a substantially constant pressure in each of the first and second chambers during a treatment session.

2. An apparatus according to claim 1, wherein the first and second pressure regulation means each include pumping means for causing a gas pressure change in a respective expansion chamber.

3. An apparatus according to claim 1, further including first and second liquid detection means, respectively connected to the first and second expansion chambers, for detecting high and low liquid levels in each of the expansion chambers.

4. An apparatus according to claim 1, wherein the first and second pressure regulation means each include means for varying a volume of a corresponding expansion chamber as a function of a liquid volume variation therein.

5. Apparatus according to claim 4, further including means for causing pressures in the first and second expansion chambers to be respectively less than and greater than atmospheric pressure, and wherein the means for varying the volume of the expansion chambers includes two variable-volume bellows chambers closed off from the atmosphere and each being connected to one of the first and second expansion chambers, the apparatus further comprising means, balanced about a pivot, for mechanically coupling the bellows chambers.

6. An apparatus according to claim 4, further comprising pressurizing means, connected to the expansion chamber, for varying gas pressure in the expansion chamber.

7. An apparatus according to claim 4, wherein the means for varying the volume of the expansion chamber includes a variable-volume chamber which is closed relative to the atmosphere and connected to the expansion chamber, the volume varying means also including actuator means for varying a volume of the variable-volume chamber as a function of liquid volume variations in the expansion chamber.

8. An apparatus according to claim 7, wherein the variable-volume chambers connected to the first and second blood expansion chambers are connected to each other mechanically and are also each connected to the actuator means for permitting the volumes of the variable-volume chambers to vary simultaneously and in the same direction.

9. An apparatus according to claim 7, wherein each variable-volume chamber has a flexible wall including bellows.

10. An apparatus according to claim 7, further including a sterile filter interposed between each of the first and second expansion chambers and a corresponding variable-volume chamber.

11. An apparatus according to claim 7, wherein the variable-volume chamber includes a moving wall which is reciprocally displaceable by the actuator means, the moving wall being displaceable in a first direction during a blood withdrawal stage, and being displaceable in a second direction, opposite to the first direction, during a blood return stage.

12. An apparatus according to claim 11, wherein the actuator means includes a rotary motor, and a connecting rod connected between the moving wall of the variable-volume chamber and the rotary motor.

13. An apparatus according to claim 12, wherein the motor is rotatable in two directions and the actuator means includes two end-of-stroke contacts to limit rotation of the motor in each direction to less than one turn.

14. A blood treatment apparatus having a circuit for circulating blood outside the body and designed to be connected to a patient via a single needle, the apparatus comprising:

a blood treatment device;
blood circulation means for causing blood to flow through the circuit;
a blood expansion chamber connected downstream of the blood treatment device for temporarily storing a volume of treated blood;
pressure regulation means connected to the blood expansion chamber for adjusting pressure in the blood expansion chamber; and
means for controlling the pressure regulation means to maintain a substantially constant pressure in the expansion chamber during a treatment session.

15. An apparatus according to claim 14, wherein the pressure regulation means includes pumping means connected to the expansion chamber to vary gas pressure in the expansion chamber.

16. An apparatus according to claim 14, wherein the variable-volume chamber has a flexible wall including bellows.

17. An apparatus according to claim 14, further including a sterile filter interposed between the expansion chamber and the variable-volume chamber.

18. An apparatus according to claim 14, further including liquid detection means connected to the expansion chamber for detecting high and low liquid levels in the expansion chamber.

19. An apparatus according to claim 14, wherein the pressure regulation means includes means for varying the volume of the expansion chamber as a function of liquid volume variations therein.

20. An apparatus according to claim 19, wherein the means for varying the volume of the expansion chamber includes a variable-volume chamber which is closed relative to the atmosphere and connected to the expansion chamber, the volume varying means also including actuator means for varying a volume of the variable-volume chamber as a function of liquid volume variations in the expansion chamber.

21. An apparatus according to claim 20, further including pressurizing means connected to the expansion chamber to vary gas pressure in the expansion chamber.

22. An apparatus according to claim 20, wherein the variable-volume chamber includes a moving wall which is reciprocally displaceable by the actuator means, the moving wall being displaceable in a first direction during a blood withdrawal stage, and being displaceable in a second direction, opposite to the first direction, during a blood return stage.

23. An apparatus according to claim 22, wherein the actuator means includes a rotary motor, and a connecting rod connected between the moving wall of the variable-volume chamber and the rotary motor.

24. An apparatus according to claim 23, wherein the rotary motor is rotatable in two directions, and the actuator means includes two end-of-stroke contacts to limit rotation of the motor in each direction to less than one turn.

25. A blood treatment apparatus having a circuit for circulating blood outside the body and designed to be connected to a patent via a single needle, the apparatus comprising:

a blood treatment device;
blood circulation means for causing blood to flow through the circuit;
a first blood expansion chamber located in the circuit upstream of the blood treatment device for temporarily storing a volume of blood to be treated;

a second blood expansion chamber located in the circuit downstream of the blood treatment device for temporarily storing a volume of treated blood; and means for maintaining a substantially constant blood flow rate through the blood treatment device.

26. An apparatus according to claim 25, wherein the means for maintaining a substantially constant blood flow rate through the blood treatment device includes pressure regulation means for maintaining substantially constant pressures in the expansion chambers, and means for maintaining the pressure in the upstream expansion chamber at pressure higher than a pressure in the downstream expansion chamber.

27. An apparatus according to claim 26, wherein the pressure regulation means includes two pumps, each pump being connected to one of the first and second expansion chambers to vary expansion chamber pressures.

* * * * *

UNITED STATES PATENT AND TRADEMARK OFFICE
CERTIFICATE OF CORRECTION

PATENT NO. : 5,227,049

DATED : July 13, 1993

INVENTOR(S) : Jacques CHEVALLET et al.

It is certified that error appears in the above-identified patent and that said Letters Patent is hereby corrected as shown below:

Title page, col. 1, Inventors, lines 4-5, change "all of Sweden" to --both of Sweden--.

Claim 25, col. 10, line 61, change "patent" to --patient--.

Signed and Sealed this

Twenty-ninth Day of March, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,227,049
DATED : July 13, 1993
INVENTOR(S) : Jacques CHEVALLET ET AL.

It is certified that error appears in the above-indentified patent and that said Letters Patent is hereby corrected as shown below:

Title page, after "Assignee: Hospal Industrie, France", please add --and Gambro AB, Sweden--.

Signed and Sealed this

Seventh Day of February, 1995

Attest:

BRUCE LEHMAN

Attesting Officer        *Commissioner of Patents and Trademarks*